United States Patent [19]
Fowler

[11] Patent Number: 5,807,282
[45] Date of Patent: Sep. 15, 1998

[54] ENDOMETRIAL TISSUE CURETTE AND METHOD

[75] Inventor: Robert Stuart Fowler, Scottsdale, Ariz.

[73] Assignee: Mayo Foundation for Medical Education and Research, Rochester, Minn.

[21] Appl. No.: 580,146

[22] Filed: Dec. 28, 1995

[51] Int. Cl.[6] ..................................................... A61B 5/00
[52] U.S. Cl. ........................................................... 600/571
[58] Field of Search .................................. 600/562, 570, 600/571, 572; 606/167, 170

[56] References Cited

U.S. PATENT DOCUMENTS

| | | |
|---|---|---|
| 3,661,144 | 5/1972 | Jensen et al. . |
| 3,670,732 | 6/1972 | Robinson . |
| 4,055,167 | 10/1977 | Bernstein . |
| 5,030,201 | 7/1991 | Palestrant ................................... 604/22 |
| 5,069,224 | 12/1991 | Zinnanti, Jr. ............................. 128/752 |
| 5,217,024 | 6/1993 | Dorsey et al. ........................... 600/570 |

OTHER PUBLICATIONS

Brochure, Zinnanti Surgical Instruments, Inc., "Endometrial Curettes", ZSI–105, Apr. 1993.
Article, "Endometrial Sampling Techniques for the Office", Koonings and Grimes, AFP, Oct. 1989.
Article, "A randomized comparison of the Pipelle, Accurette, and Explora endometrial sampling devices", Lipscomb et al., Am J Obstet Gynecol, vol. 170, No. 2 1993.
Article, "The Pipelle: A disposable device for endometrial biopsy", Cornier, Am. J. Obstet. Gynecol., vol. 148, No. 1 1984.
Article, "A new method of endometrial cytological sampling—the Gynoscann: a comparison with Vabra curettage", Kovacs et al., The Medical Journal of Australia, vol. 148, May 16, 1988.
Article, "Office Diagnosis of Endometrial Carcinoma", Regan and Isaacs, Primary Care & Cancer, Jan. 1992.
Article, "Clinical Evaluation of the Pipelle Endometrial Suction Curette for Timed Endometrial Biopsies", Check et al., Journal of Reproductive Medicine, vol. 34, No. 3, Mar. 1989.
Article, "Diagnostic Endometrial Aspiration with the Karman Cannula", Suarez et al., The Journal of Reproductive Medicine, vol. 28, No. 1, Jan. 1983.
Article, "Endometrial Biopsy", Staff Meetings of the Mayo Clinic, pp. 143–144, meeting Feb. 13, 1935.

*Primary Examiner*—Max Hindenburg
*Attorney, Agent, or Firm*—Gregory F. Cotterell

[57] ABSTRACT

A uterine curette device and method for curetting the endometrial lining the uterus using a cannula having a hollow curetting head including at least one longitudinal slot through which endometrium can be suctioned into the curetting head. The at least one longitudinal slot having two margins with at least one margin having a curetting edge where the margin meets the outer surface of the curetting head. Endometrium is curetted by rotating the cannula about its longitudinal axis so that the at least one curetting edge curettes off the endometrial sample which is then suctioned into the cannula.

45 Claims, 3 Drawing Sheets

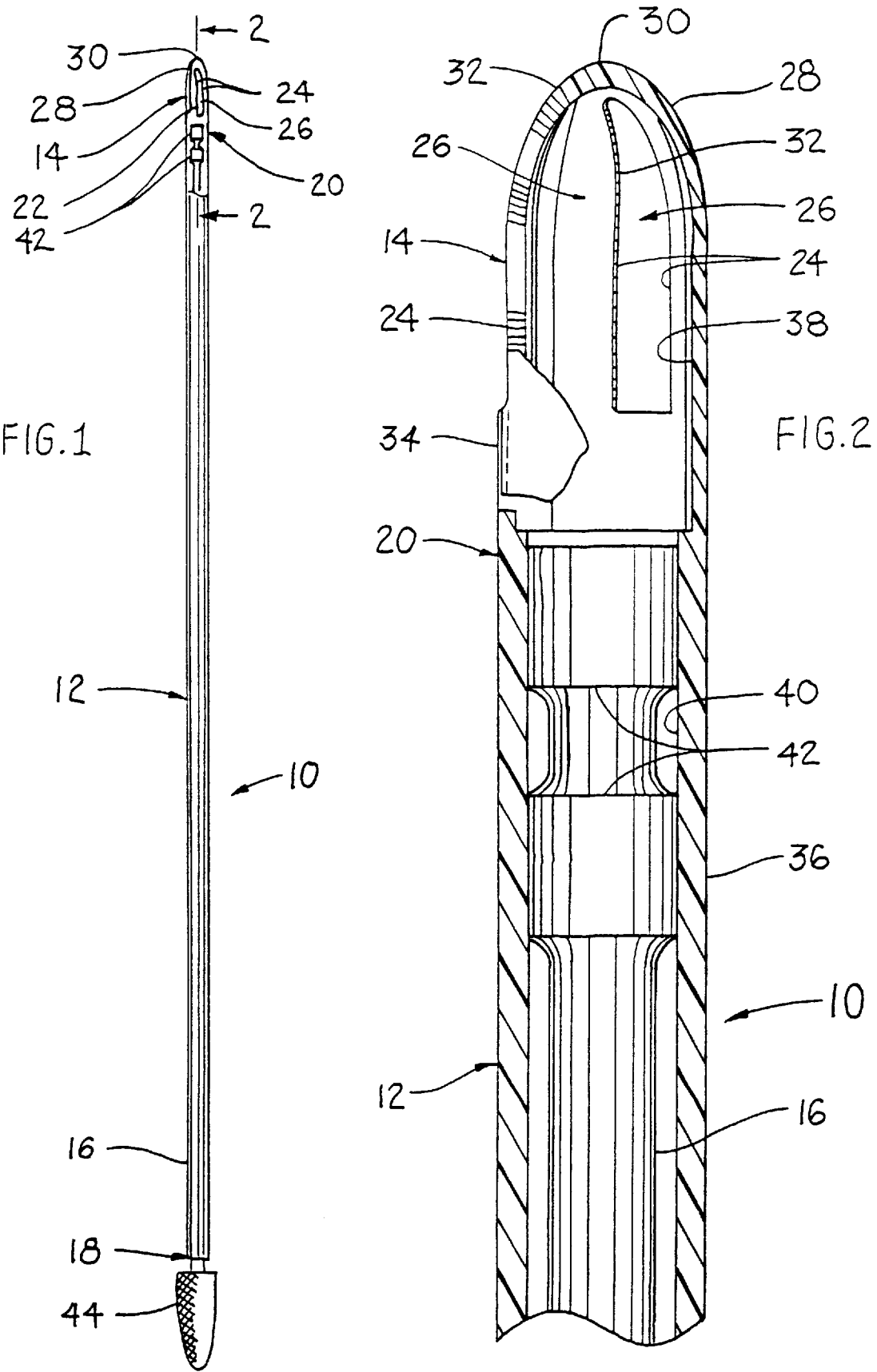

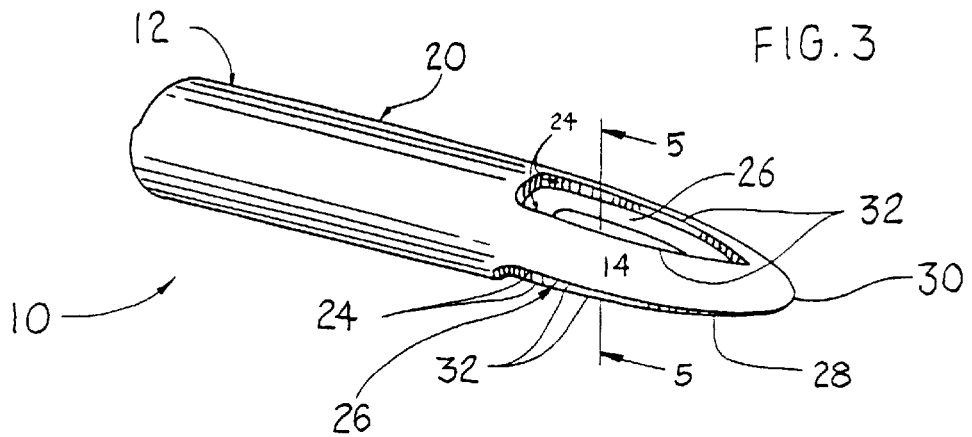
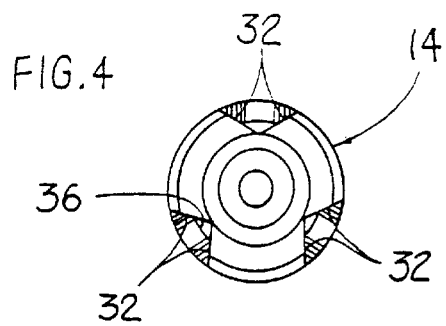
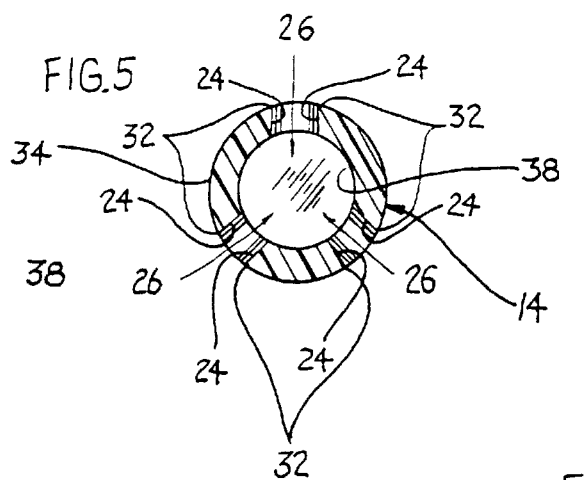
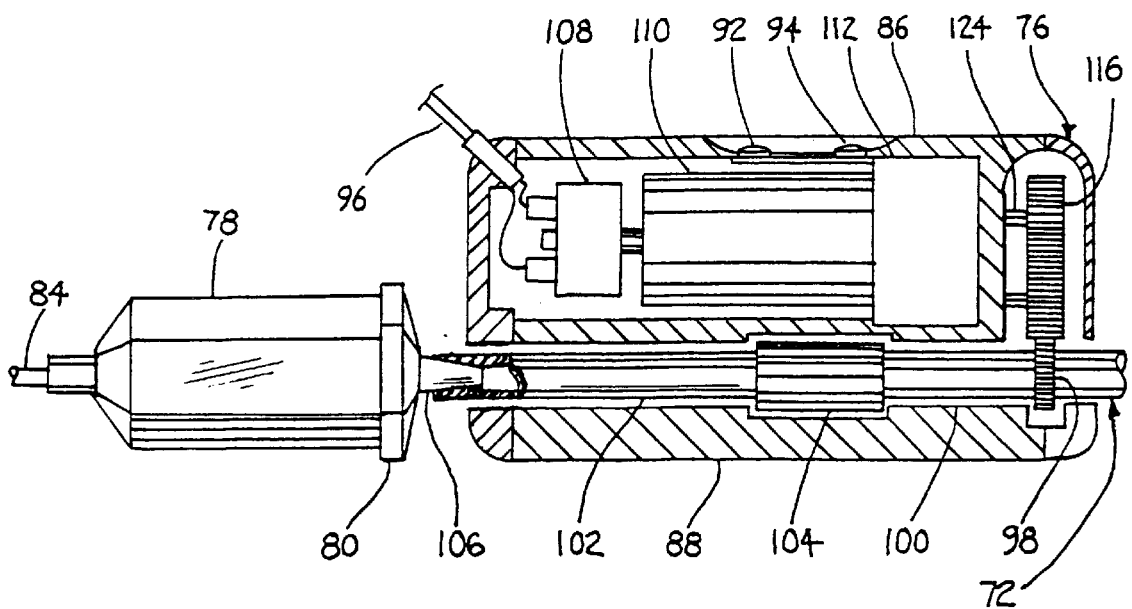

ENDOMETRIAL TISSUE CURETTE AND METHOD

FIELD OF THE INVENTION

The present invention pertains to an endometrial curette and, in particular, an endometrial curette requiring minimal to no dilatation of the cervix.

BACKGROUND OF THE INVENTION

Curettage of the endometrial lining of the uterus is often indicated to evaluate abnormal uterine bleeding. It is principally a diagnostic procedure to rule out pre-cancer and cancerous change. However, it does confer therapeutic effect in some cases. The lining of the uterus, known as the endometrium, responds to hormonal influences as part of the normal and abnormal endocrine patterns found in females. The uterine lining undergoes proliferative change in response to estrogen or tamoxifen, secretory change in response to progestins, or atrophic change in the absence of all hormonal stimuli. During the natural cycle, in response to ovarian hormone secretion, the uterus undergoes proliferative response to estrogen, subsequently followed by a secretory response to estrogen plus progestin secretion. If pregnancy is not established, ovarian secretion of both the hormones declines resulting in sloughing of the endometrial lining, otherwise known as a menstrual period.

This endometrial cycling begins with menarche and ceases with menopause. Various conditions during the pre-menopausal and postmenopausal years cause the uterine lining to undergo abnormal proliferative changes requiring diagnostic intervention through curettage of the endometrium. The traditional surgical intervention known as dilatation and curettage (D&C) involves dilatation of the cervical canal and curetting of the endometrial lining of the uterus. Dilatation is accomplished using progressively wider uterine sounds to permit insertion of the uterine curettes.

In the United States the nearly universal practice is to perform the curettage with Sims Curettes, which range from 7 top 10 mm. The average diameter of the non-gravid cervix measures less than 4 mm in diameter. Consequently, the cervical canal requires dilatation to about twice its average non-gravid diameter. To accomplish dilatation of the cervix, a substantial force must be applied along the longitudinal axis of the cervical canal. This requires application of a tenaculum to the periphery of the cervix to apply the necessary countertraction. This procedure is exquisitely painful in the majority of unanesthetized patients because of the high concentration of stretch receptors in the cervix.

The curettage is accomplished by inserting the curette within the uterine cavity to the apex, applying force to the curette blade in a direction perpendicular to the uterine wall, dragging the curette in a longitudinal fashion from the fundus to the lower uterine segment, and then out the cervical canal. The longitudinal forces applied during a curettage place the broad ligaments, cardinal ligaments, and uterosacral ligaments on a stretch. The pain accompanying the longitudinal forces applied during curettage likely result from stretching the broad ligament, cardinal ligaments, and uterosacral ligaments. The suspensory ligaments of the uterus and cervix are innervated via fibers following the sympathetic nervous system pathways. Due to the diffuse origin of these pain fibers, it is difficult to anesthetize the suspensory ligaments with local techniques. Therefore, most women require some level of monitored anesthesia to accomplish this procedure.

Anesthetic techniques to relieve the pain in ascending order of effectiveness include IV sedation, paracervical block, regional anesthesia such as epidural or spinal block, and general anesthesia. With the limited effectiveness of IV sedation and paracervical block, and the prolonged recovery time associated with regional anesthesia, the vast majority of D&Cs are accomplished by general anesthesia. Eliminating the dilatation procedure could circumvent the need for monitored anesthesia. The combination of both dilatation and curettage generally precludes having only local anesthetic intervention.

Up to the present time, the D&C has been considered the "gold standard" for gynecological intervention for the diagnosis of endometrial disease states. Along with its ability to remove the majority of the endometrium, providing accurate diagnostic sensitivity, the procedure unfortunately requires the expense of outpatient surgical facilities and monitored anesthesia. Attention has been focused on developing instruments that are equal to or of better diagnostic accuracy, but do not require cervical dilatation lending themselves to inexpensive and convenient office procedures.

As far back as the 1930s, beginning with Drs. Novak and Randall, office devices consisting of 1 to 4 mm stainless steel curettes with smooth oval aperture or elongated aperture with serrated edges were proposed for office endometrial sampling. Although several favorable studies have been reported regarding their success in obtaining adequate samples, the technique was limited by relying on rigid stainless steel, which does not lend itself to conforming to the normal anatomic curves of the uterine cavity. This results in greater discomfort. In addition, the adequacy of the sampling thoroughness is limited by poor suction techniques using glass or plastic syringes attached to the proximal end.

Subsequently, in 1970, Jensen and Jensen marketed the Vabra® aspirator available from Berkeley Medevices, Inc., 907 Camelia Street, Berkeley, Calif., 94710, consisting of a 3 mm stainless cannula with a crescent aperture at the distal end coupled with a mechanical suction pump that provides a continuous suction. A number of studies show that its diagnostic sensitivity may approach that of D&C. However, the device has fallen in popularity today because it is much more painful than more recently developed techniques.

With the advent of plastic, a number of new curettes have been introduced to the market ranging from 2 to 4 mm. They fall into one of two design groups. First, the distal end of the cannula either has a small wedge taken out of the plastic resulting in a crescent aperture at the distal most end of the opening, the aperture is simply a round hole in the cannula at the distal end, or consists of a linear port. The other design variance is the source of the suction, either an internal piston exists within the cannula which can be withdrawn, thereby creating a vacuum within the cannula or the hollow cannula is attached to a mechanical suction source. Berkeley Medevices has expanded their line of Vabra® aspirator canals to include plastic 4 mm cannulas with the wedge shaped or linear port. Another company in the market of aspirators with mechanical suction is the Mylex Tissue Trap Series from Mylex Products, 5915 Northwest Highway, Chicago, Ill., 60631, that have 2 and 3 mm stainless, as well as 3 to 7 mm flexible plastic, 3 to 7 mm semirigid, and 8 to 12 mm rigid plastic cannulas.

The latest devices consist of 3 mm plastic canmulas with an internal piston for suction, and a round hole aperture at the most distal end of the cannula. First to be introduced in the United States is the Pipelle de Cornier™ which was developed in France and marketed in the United States as Pipelle® by Unimar Corporation, 475 Danbury Road, Wilton, Conn., 06897. Other companies have produced nearly identical instruments with minor variations on the theme regarding the type of plastics used and the specific design of the internal piston rod. One such device is the subject of the U.S. Pat. No. 5,069,224 issued to Zinnanti, Jr., and discloses an endometrial sampler that obtains small bits or portions of endometrium by aspiration without cutting but rather avulsing the tissue sample. Other examples include: the Gyno Sampler by GynoPharma, Inc., 50 Division Street, Somerville, N.J., 08876, having a product code 164-25; the Endocell by Wallach Devices, Inc., 291 Pepe's Farm Road, Milford, Conn., 06460; and the Endosampler by Medgyne Products, Inc., 328 North Eisenhower Lane, Lombard, Ill., 60148. These devices are manipulated by an in and out motion with concurrent rotation and the endometrium is aspirated into the round aperture. The device is then withdrawn from the uterus along the longitudinal axis while the aspirated tissue remains within the cannula. These devices address the problems associated with the need for cervical dilatation associated with the traditional curettage with Sims Curettes.

The limitation of these devices is that they rely on a very small aperture to remove the endometrium. Additionally, the mechanical action is simply one of aspiration only at the site where the port comes in contact with the endometrial lining. An article by Rodriguez in *American Journal of Obstetrics and Gynecology,* January 1993, indicates that only four percent of the endometrial lining is removed even when the Pipelle is used in sequence three times. By comparison, the Vabra® aspirator is more thorough removing approximately 42 percent of the uterine lining. However, both techniques are far from removing the vast majority of endometrium provided by a traditional D&C. Consequently, these devices have substantial risk of missing endometrial disease such as hyperplasia or cancer. By only removing a small portion of endometriur, these devices preclude realizing any possible therapeutic gain by removing the majority of the dysfunctional endometrial lining.

It would be desirable to have a device that would be capable of removing substantially all of the endometrium avoiding the risk of missing an important diagnosis, without causing a significant amount of pain and discomfort because of dilatation of the cervix and traction, tugging and pulling on the uterus.

SUMMARY OF THE INVENTION

The present invention is an endometrial tissue curette for use in a uterus to remove the endometrial tissue lining of the uterus, the curette comprising a cannula, the walls of which define a substantially elongate cylindrical hollow bore and having an open proximal end and a distal end along the longitudinal axis of the cannula, the distal end including a longitudinally elongate hollow curetting head having an outside surface and a hollow inside in direct communication with the hollow bore, the curetting head having at least one substantially longitudinally elongate slot comprising at least two substantially longitudinal margins defining a space there between and through the hollow curetting head and providing a direct communication from the hollow inside to the outside of the elongate hollow curetting head, at least one curetting edge formed on at least one of the at least two substantially longitudinal margins at the outside surface, and an elongate rod of smaller diameter than the cylindrical hollow bore and slidably positionable within the cylindrical hollow bore of the cannula, the rod having a proximal end and a distal end, the proximal end of the rod extending out the open proximal end of the cannula, the proximal end of the rod ending in a handle suitable for grasping by an operator, the rod having at least one piston at the distal end of the rod in slidable sealable engagement with the cylindrical hollow bore so that withdrawing the rod away from the distal end of the cannula draws suction in the cylindrical bore at the at least one slot drawing an endometrial tissue sample into the space between the at least two margins whereby rotating the cannula around the long axis rotates the at least one curetting edge curetting the tissue sample free from the uterus and suctioning the tissue sample into the cylindrical hollow bore.

The present invention accomplishes the important objective of removing a significant majority of the uterine endometrial lining avoiding the risk of missing an important, such as cancer or pre-cancerous conditions.

Additionally, the present invention substantially reduces the level of pain and discomfort experienced by the patient because the need to dilate the cervix to gain access to the uterine cavity is eliminated or sufficiently minimized as to not warrant significant anesthetic intervention.

Another object of the present invention is to provide various configurations and numbers of longitudinal blades on the curetting head. The present invention anticipates having one or more slots having one or two curetting edges per slot. The placement of curetting edges also provides unidirectional and bi-directional rotation of the curetting head increasing control over the curetting action.

An additional object of the present invention is the ability to be manually rotated using a piston and rod to generate adequate suction so that an operator may perform adequate curettage without the need for a power source and a vacuum source.

Alternatively, it is an additional objective to provide a motorized curette having directional and rotational control that will substantially increase the speed with which the procedure may be completed.

The above and other objects and advantages of the present invention become more readily apparent when reference is made to the following detailed description taken in conjunction with the accompanying drawings, and are in no way intended limit the scope of the present invention.

BRIEF DESCRIPTION OF THE DRAWINGS

FIG. 1 is a side elavational view of an embodiment of the present invention;

FIG. 2 is an enlarged central section through the distal cannula and cutting head end of the embodiment of the invention as seen generally along the line 2—2 of FIG. 1;

FIG. 3 is a perspective view of the distal cannula end and cutting head of the embodiment of the present as seen generally in FIG. 1;

FIG. 4 is a distal end elevational view of the cutting head end of the embodiment of the present invention as generally seen in FIG. 1;

FIG. 5 is sectional view taken at the line 5—5 in FIG. 3;

FIG. 8 is an enlarged central section through the motor drive unit of the additional alternate embodiment as generally in FIG. 7 along the line 8—8 in FIG. 7.

DETAILED DESCRIPTION OF THE INVENTION

Figure 7:
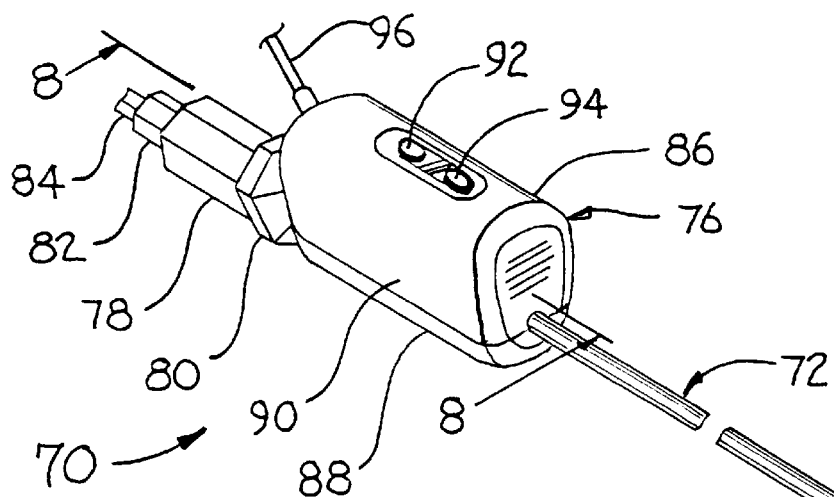
FIG. 7 is a perspective view of an additional alternate embodiment of the present invention.

As seen in FIG. 1, an endometrial tissue curette 10 is disclosed. Endometrial tissue curette 10 comprises a cannula 12, a hollow curetting head 14, and a rod 16. Cannula 12 comprises a proximal end 18, and a distal end 20 which is opened and through which rod 16 is placed, substantially traversing the length of the inside of cannula 12.

FIGS. 2, 3, 4 and 5 in conjunction with FIG. 1 disclose a preferred embodiment of the present invention in hollow curetting head 14 comprising a plurality of longitudinal slots 22, and specifically in this embodiment there are three longitudinal slots 22, a curetting head tip 30 at the distal most end of endometrial tissue curette 10, a curetting head outer surface 34 substantially continuous with a cannula outer surface 36, and a curetting head inner surface 38 substantially continuous with a cannula inner surface 40.

Each longitudinal slot 22 comprises at least two substantially longitudinal slot margins 24 which in turn define a longitudinal slot space 26 through which the hollow chamber of hollow curetting head 14 may directly communicate from curetting head inner surface 38 to curetting head outer surface 34 and in turn is in direct communication with the inside space of cannula 12.

At least one of the plurality of slot margins 24 will have a curetting edge 32 at the junction of slot margin 24 with curetting head outer surface 34. Any one or number of slot margins 24 may have an associated curetting edge 32 and in the preferred embodiment having three longitudinal slots 22 with a corresponding six longitudinal slot margins 24 there are six corresponding curetting edges 32. It is anticipated by the present invention that there may be any number of longitudinal slots placed within a curetting head such that there may be a number of curetting edges employed by an embodiment of the present invention.

Although not depicted in any of the figures, the present invention also anticipates that the substantially longitudinal margin of a longitudinal slot may be further modified so as to comprise leading and trailing edges wherein a trailing edge will have a slightly greater radius of curvature from the longitudinal axis than a leading edge which may substantially increase the curetting action. Additionally, the cannula may also be modified by placing a bend in the distal cannula at a point just proximal to the curetting head. The bend would be less than about 20 degrees. This bend has the added benefit of improving the curetting action, particularly for uterine cavities of unusual shape or dimension.

As depicted in FIGS. 1 and 2, rod 16 comprises pistons 42 and a rod handle 44. Rod 16 is placed through the opening at proximal end 18 of endometrial tissue curette 10 with pistons 42 at the proximal end of rod 16 and constructed so as to have the surfaces of pistons 42 in slidable abuttable position adjacent to cannula inner surface 40. Rod handle 44 at the proximal end of rod 16 provides a means for withdrawing rod 16 and pistons 42 along the length of cannula inner surface 40 such that a vacuum is created within cannula 12 and hollow cavity of hollow curetting head 14 distal to pistons 42.

Figure 6:
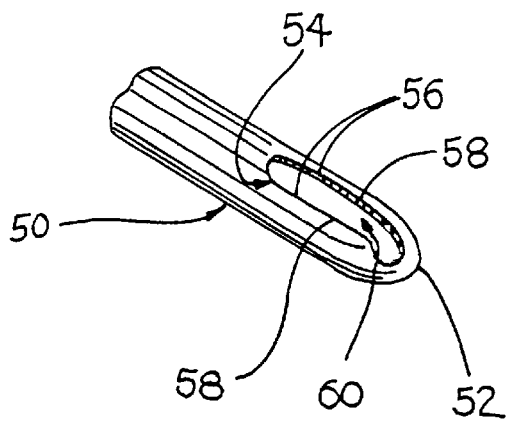
FIG. 6 is a perspective view of a cutting head in an alternate embodiment of the present invention.

FIG. 6 depicts an alternative embodiment of the present invention as a curetting head 50 comprising a distal tip 52 and a single longitudinal slot 54. Longitudinal slot 54 comprises two longitudinal slot margins 56. Either or both of the longitudinal slot margins 56 may have an associated curetting edge 58. Longitudinal slot margins 56 define a slot space 60. Like curetting head 14 of FIGS. 1 through 5, curetting head 50 defines a hollow chamber that directly communicates through slot space 60 to the outside and directly to the hollow space of the cannula, not depicted in this figure. The present invention anticipates alternative configurations of curetting heads having one or more longitudinal slots, each slot having two margins whereby at least one margin, if not both, will carry a curetting edge.

The present invention anticipates the use of all biocompatible materials and other materials suitable for use as surgical instruments. Such characteristics usefil for constructing an endometrial tissue curette according to the present invention include those materials that provide one or more of following characteristics: To be sterilized, molded, casted, sharpened, flexed, polished and/or used in multiple procedures. The present invention anticipates a preferred embodiment wherein the cannula and curetting head are fashioned or constructed from the same polymeric material such as ejection molded thermoplastics. Clinical studies of the safety and efficacy of this device have demonstrated useful embodiments wherein a surgical stainless steel curetting head is connected to a polymeric plastic cannula by mechanically swaging the cannula onto the proximal end of the stainless steel curetting head. There are a number of metals, alloys and polymeric plastics suitable for the construction of a device according to the present invention and these materials are well known to those skilled in the art.

Figure 9:
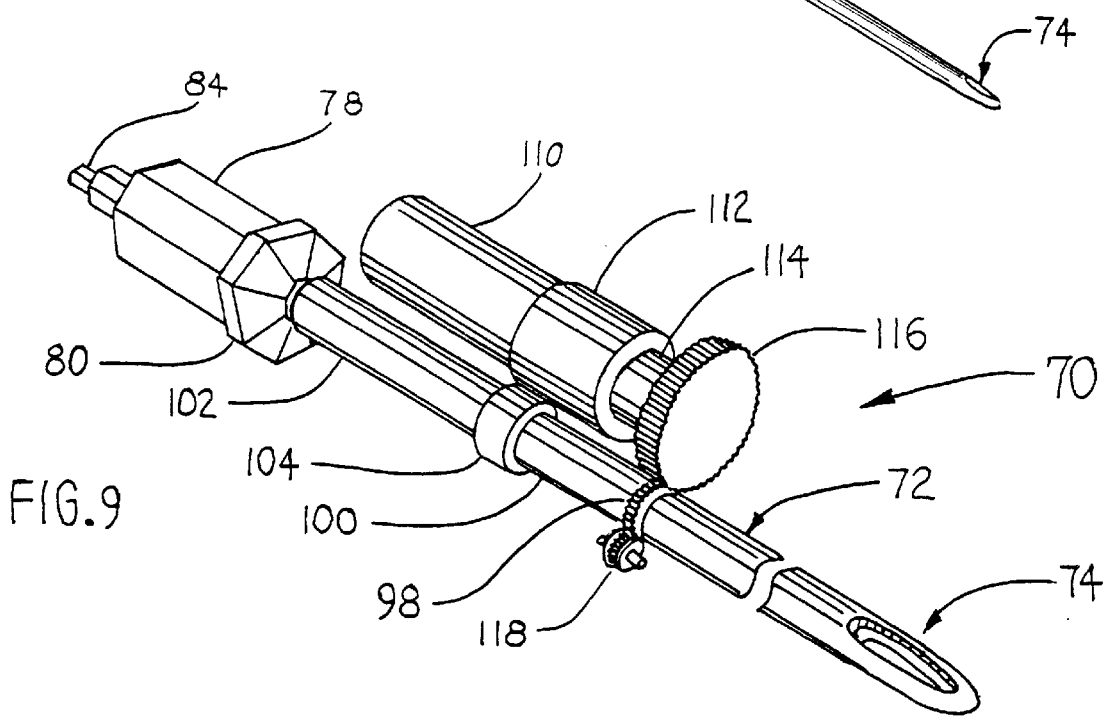
FIG. 9 is a perspective view of the additional alternate embodiment as seen generally in FIG. 7 with the outer motor housing removed for clarity.

An additional alternate embodiment of the present invention is depicted in FIGS. 7, 8 and 9 wherein an endometrial tissue curette 70 represents a motor driven embodiment of the present invention. Endometrial tissue curette 70 comprises a tubular body 72, a curetting head 74, an electric drive motor 76, a tissue trap 78 and a vacuum tube 84. As depicted in FIG. 7, electric drive motor 76 comprises an upper body housing 86, a lower body housing 88 that join at a body seam 90 using a hinge and catch mechanism, not depicted, for opening and closing electric drive motor housing 86, 88. The ability to open and close body housings 86 and 88 provides ready access to tubular body 72 for removing and replacing tubular body 72 after it is used.

Additionally, electric drive motor 76 comprises a control button 92, a control button 94, and a power cord 96 for receiving electrical energy from an appropriate electrical source, not depicted. Control buttons 92 and 94 each provide on/off capabilities as well as rotational direction and rotational speed of tubular body 72.

FIG. 8 is a mid-line cross-section through upper body housing 86 and lower body housing 88 to more clearly depict the interconnection of tubular body 72 with electric drive motor 76. In endometrial tissue curette 70, tubular body 72 comprises a driven gear 98 near a proximal end 100. Additionally, proximal end 100 is adaptable to a spin relief coupling 104 which provides adequate vacuum sealing between proximal end 100 and spin relief coupling 104 while allowing tubular body 72 to be rotated around its longitudinal axis. The vacuum connection is completed using a vacuum source adapting segment 102 adaptably connected to a trap cover coupling 106. Like tubular body 72, vacuum source adapting segment 102, spin relief coupling 104 and trap cover coupling 106 are hollow tubular structures through which a vacuum may be applied from a vacuum source, not depicted, through vacuum tube 84 and tissue trap 78.

Further depicted in FIG. 8 are other drive components of electric drive motor 76 comprising a speed and direction regulator 108, an electric motor 110, a gear reduction assembly 112, a drive shaft 114 and a drive gear 116 suitably engageable with driven gear 98 of tubular body 72. In FIG.

9 one of two idler gears 118 are additionally depicted and are suitably engageable with driven gear 98 and useful for maintaining the gear coupling between driving gear 116 and driven gear 98.

In general, the operation of the preferred embodiment of the present invention and in reference to FIGS. 1 through 5, endometrial tissue curette 10 is inserted through a cervical of a uterus. Curetting head tip 30, having a slightly rounded conformation, provides easy insertion. In conjunction with measuring marks on the side portion of cannula 12, measured from curetting head tip 30, a measurement of the uterine cavity length may be obtained when curetting head tip 30 reaches the fundus of the uterus. After insertion into the uterus, an operator grasps rod handle 44 while holding on to cannula 12 near proximal end 18. The operator then gently withdraws rod 16 from cannula 12 by holding cannula 12 stationary and pulling on rod handle 44 until piston 42 is at proximal end 18 of cannula 12. This action of withdrawing rod 16 creates a suction in cannula 12 and hollow curetting head 14. The suction acts directly through slot space 26 drawing adjacent endometrial lining into each slot space 26 between slot margins 24. The operator then rotates cannula 12 about its longitudinal axis through a twisting motion applied to cannula 12 while grasping cannula 12 near proximal end 18. The rotational movement of cannula 12 and hollow curetting head 14 provides the mechanism by which curetting edges 32 curette the endometrial lining from the uterine wall. Tissue collected from the uterine wall is suctionably drawn inside hollow curetting head 14 and distal end 20 of cannula 12. Cannula 12 is slowly withdrawn while continuing to rotate. Cannula 12 is removed from the uterus when either there is no sign of further tissue advancing up within cannula 12 or cannula 12 is filled with tissue. The tissue contents within cannula 12 and hollow curetting head 14 can then be expressed back through slot spaces 26 using a plunger action by pushing rod 16 back into canmula 12 until rod pistons 42 reach their starting positions. The operator may then re-insert cannula 12 and hollow curetting head 14 into the uterine lumen and having noted the level at which the last curetting sample was obtained may now choose a different measuring mark to proceed to repeat the above steps to obtain a new endometrial tissue specimen.

FIGS. 7, 8 and 9 depict an alternative additional embodiment of the present invention wherein, in operation, electric drive motor 76 has been adapted to construct the motor driven endometrial tissue curette 70. As disclosed and for purposes of this discussion, this alternative additional embodiment uses a curetting head 74 which is substantially similar to curetting head 14 of the preferred embodiment of the present invention disclosed in FIGS. 1 through 5. It should be understood that the present invention anticipates that this motor driven embodiment, as with the manually controlled embodiment, may use a curetting head consistent with the scope of the present invention.

Electric drive motor 76 is placed over proximal segment 100 so that drive gear 116 and idler gears 118 engage driven gear 98. This conformation is achieved when lower body housing 88 is closed and latches with upper body housing 86 along body seam 90. Vacuum source adapting segment 102 and spin relief coupling 104 are held in place and adjacent to the proximal edge of proximal segment 100. Tissue trap 78 with trap cover 80 and trap cover coupling 106 are attached to the proximal end of vacuum source adapting segment 102 to complete the assembly. A vacuum source, not depicted, is then connected to tissue trap 78 using vacuum hose 84 by inserting vacuum hose 84 into the proximal end of tissue trap 78.

Endometrial tissue curette 70 is inserted beginning with curetting head 74 to a distance within the uterine lumen determined and chosen by the operator. Typically, the operator starts with the curetting head at the uterine fundus. This distance can be measured by using measurement scribes along the length of tubular body 72 as measured from the tip of curetting head 74.

Following insertion of curetting head 74 and the distal portion of tubular body 72, the vacuum source is then activated creating a vacuum through the tissue trap and hollow bores from vacuum source 84 through vacuum adapting segment 102, spin relief coupling 104, proximal segment 100, tubular body 72 and curetting head 74. The effect of the presence of a vacuum is to create a suction at the slot spaces of curetting head 74 just as a suction was created at slot spaces 26 depicted in FIGS. 1 through 5. Endometrial tissue is then drawn into the space between the slot margins of curetting head 74 and the operator may now activate drive motor 76 by depressing either control switch 92 or 94. Depression of the control switches 92, 94 provides both rotational direction and rotational speed. Control switches 92, 94 in conjunction with speed and direction regulator 108 use electrical switching and circuitry conventional to those skilled in the art for providing reverse switching and variable speed. The ability to choose both speed and direction of rotation provides an operator considerable latitude in choosing an endometrial curette with different configurations to the curetting head consistent with the present invention. It is anticipated by the present invention that there may be one or more slots with two or more margins and that there may be one or more curetting edges created at the junction of one or more margins to the outer surface of a curetting head. Additionally, it is anticipated that a slot and the associated two margins may have a designated trailing margin and a leading margin such that the curetting edge may be created at the juncture of the trailing margin with the outer surface with the radius of the curetting edge being greater than the radius of the junction of the leading margin with the outer surface. This construction would create a curetting head having a curetting action preferred by one direction of rotation and not the reverse. A unidirectional curetting head so constructed would have improved curetting ability over bi-directionally constructed curetting heads as a direct result of the trailing curetting edge being elevated above the leading margin.

With activation of electric motor 76, rotation of tubular body 72 and curetting head 74 results in curetting endometrial tissue from the uterine wall. Vacuum applied through vacuum hose 84 creating the suction at curetting head 74 draws the curetted endometrial tissue into the hollow bore of curetting head 74 and tubular body 72 and through proximal segment 100, spin relief coupling 104, and vacuum source adapting segment 102, through trap cover coupling 106 and depositing the endometrial tissue inside of tissue trap 78. While holding down either control switch 92 or 94 the operator may slide tubular body 72 and curetting head 74 inward and outward through the uterine cavity continuously curetting endometrial tissue from the uterine lining and collecting the curetted tissue in tissue trap 78. If equipped with a bi-directional cutting head, the operator may choose to reverse direction of the electric motor and cannula rotation to insure adequate curett age, especially in cases of uterine cavity irregularity. When the operator is satisfied that curetting has been maximially achieved, the operator releases control switches 92, 94 and withdraws the device.

The endometrial tissue sample collected in tissue trap 78 is easily removed by removing trap cover coupling 106 from vacuum source adapting segment 102 and then removing tissue trap cover 80 from tissue trap 78 to gain access to the collected tissue. Electric drive motor 76 may be opened at body seam 90 and the various portions of the device including tubular body 72, proximal segment 100, spin relief coupling 104 and vacuum source adapting segment 102 may be removed and replaced by new components.

The present invention substantially improves the overall surgical intervention for performing uterine endometrial curettage. Dilatation of the cervix is not necessary, or is required only minimally, and the endometrial sample is a significant majority of all of the endometrium. Patient comfort is maximized along with patient acceptance without running a risk of missing a significant diagnosis, such as cancer, because the sample size was too small. Patients and third party payors will realize a substantial savings in costs because expensive anesthesia support and potential need for hospitalization following general anesthesia are no longer necessary.

The foregoing description is considered as illustrative only of the principles of the invention, and since numerous modifications and changes will readily occur to those skilled in the art, it is not desirable to limit the invention to the exact construction and operation shown and described. Accordingly, all suitable modifications and equivalents may be resorted to, falling within the scope of the present invention.

I claim:

1. An elongate hollow cylindrical endometrial tissue curette for removing an endometrial tissue lining a uterus, the curette comprising:

a longitudinally elongate hollow curetting head, at a distal end of the curette, having an outside surface extending longitudinally to a substantially rounded tip and an inside surface defining a hollow interior, the curetting head having at least one substantially longitudinally elongate slot with at least a portion of the at least one elongate slot extending into the substantially rounded tip, the at least one elongate slot comprising at least two substantially longitudinal margins defining a space there between and through the hollow curetting head and providing a direct communication from the hollow interior to the outside of the elongate hollow curetting head, at least one curetting edge formed on at least one of the at least two substantially longitudinal margins at the outside surface; and suction means for creating a suction in the hollow curetting head at the at least one elongate slot to suctionably draw an endometrial tissue sample into the space between the at least two margins;

whereby rotating the elongate hollow cylindrical endometrial tissue curette around its longitudinal axis rotates the at least one curetting edge curetting the tissue sample free from the lining of the uterus and suctioning the tissue sample into the hollow curetting head.

2. The endometrial tissue curette of claim 1 in which the curette is made of a single material.

3. The endometrial tissue curette of claim 2 in which the material is a synthetic polymeric plastic material.

4. The endometrial tissue curette of claim 2 in which the material is surgical grade stainless steel.

5. The endometrial tissue curette of claim 1 in which the curetting head includes a proximal portion having a bend in the longitudinal axis.

6. The endometrial tissue curette of claim 5 in which the bend is less than about 20°.

7. The endometrial tissue curette of claim 1 in which one of the at least two margins is a leading margin and the other margin is a trailing margin, the leading margin having a radius from a central longitudinal axis of the curetting head which is shorter than a radius of the trailing margin.

8. The endometrial tissue curette of claim 7 in which the at least one curetting edge is formed on the trailing margin at the outer surface.

9. The endometrial tissue curette of claim 1 in which a curetting edge is formed on each margin at the outside surface.

10. The endometrial tissue curette of claim 1 in which there are three substantially longitudinal elongate slots.

11. The endometrial tissue curette of claim 10 in which six curetting edges are formed, one curetting edge on each of the six margins at the outside surface.

12. The endometrial tissue curette of claim 3 in which the suction means comprises an elongate rod slidably positionable within the cylindrical hollow bore of the curette, the rod having a proximal end and a distal end, the proximal end of the rod extending out an open proximal end of the curette, the proximal end of the rod ending in a handle suitable for grasping by an operator, the rod having at least one piston at the distal end of the rod in slidable sealable engagement with the cylindrical hollow bore so that withdrawing the rod draws the at least one piston away from the hollow curetting head creating the suction.

13. The endometrial tissue curette of claim 12 in which the rod and at least one piston are made of the same synthetic polymeric plastic material as the curette.

14. The endometrial tissue curette of claim 12 which the rod and at least one piston are made of a dissimilar synthetic polymeric plastic material from that of the curette.

15. The endometrial tissue curette of claim 1 in which the suction means comprises a vacuum source and tube connectable to an open proximal end of the curette to create the suction.

16. The endometrial tissue curette of claim 1 further comprises rotation means for rotating the curette around its longitudinal axis.

17. The endometrial tissue curette of claim 16 in which the rotation means comprises an electrical motor mechanically engageable with a driven gear attached near the proximal end of the curette.

18. The endometrial tissue curette of claim 17 in which the rotation means comprises a spin relief coupling proximal to the driven gear and the suction means comprises a vacuum source and tube connectable to an open proximal end of the curette to create the suction.

19. The endometrial tissue curette of claim 1 in which the curette has an outside diameter of about 4 millimeters.

20. The endometrial tissue curette of claim 1 in which the curette has an outside diameter of less than about 4 millimeters.

21. The endometrial tissue curette of claim 1 in which each at least one substantially longitudinal elongate slot has a maximum transverse width less than the inside diameter of the elongate hollow cylindrical endometrial tissue curette.

22. An endometrial tissue curette for removing an endometrial tissue lining a uterus, the curette comprising:

a cannula defining an elongate cylindrical hollow bore and having an open proximal end and an open distal end along the longitudinal axis of the cannula;

a longitudinally elongate hollow curetting head at the distal end of the cannula, having an outside surface extending longitudinally to a substantially rounded tip and a hollow interior in direct communication with the hollow bore, the curetting head having at least one substantially longitudinally elongate slot with at least a portion of the at least one elongate slot extending into the substantially rounded tip, the at least one elongate slot comprising at least two substantially longitudinal margins defining a space there between and through the hollow curetting head and providing a direct communication from the hollow interior to the outside of the elongate hollow curetting head, at least one curetting edge formed on at least one of the at least two substantially longitudinal margins at the outside surface; and suction means for creating a suction in the cylindrical bore and the interior of the curetting head at the at least one slot to suctionably draw an endometrial tissue sample into the space between the at least two margins;

whereby rotating the cannula around the cannula longitudinal axis rotates the at least one curetting edge curetting the tissue sample free from the lining of the uterus and suctioning the tissue sample into the cylindrical hollow bore.

23. The endometrial tissue curette of claim 22 in which the cannula and curetting head are a single piece of material.

24. The endometrial tissue curette of claim 23 in which the material is a synthetic polymeric plastic material.

25. The endometrial tissue curette of claim 23 in which the material is surgical grade stainless steel.

26. The endometrial tissue curette of claim 22 in which the cannula and curetting head are made of dissimilar materials.

27. The endometrial tissue curette of claim 26 in which the cannula is made of a synthetic polymeric plastic material and the curetting head is made of surgical grade stainless steel.

28. The endometrial tissue curette of claim 22 in which one of the at least two margins is a leading margin and the other margin is a trailing margin, the leading margin having a radius from a central longitudinal axis of the curetting head which is shorter than a radius of the trailing margin.

29. The endometrial tissue curette of claim 28 in which the at least one curetting edge is formed on the trailing margin at the outer surface.

30. The endometrial tissue curette of claim 22 in which a curetting edge is formed on each margin at the outside surface.

31. The endometrial tissue curette of claim 22 in which there are three substantially longitudinal elongate slots.

32. The endometrial tissue curette of claim 31 in which six curetting edges are formed, one curetting edge on each of the six margins at the outside surface.

33. The endometrial tissue curette of claim 24 in which the suction means comprises an elongate rod slidably positionable within the cylindrical hollow bore of the cannula, the rod having a proximal end and a distal end, the proximal end of the rod extending out the open proximal end of the cannula, the proximal end of the rod ending in a handle suitable for grasping by an operator, the rod having at least one piston at the distal end of the rod in slidable sealable engagement with the cylindrical hollow bore so that withdrawing the rod draws the at least one piston from the distal end of the cylindrical rod creating the suction.

34. The endometrial tissue curette of claim 33 in which the rod and at least one piston are made of the same synthetic polymeric plastic material as the cannula and curetting head.

35. The endometrial tissue curette of claim 33 which the rod and at least one piston are made of a dissimilar material from that of the cannula.

36. The endometrial tissue curette of claim 22 in which the suction means comprises a vacuum source and tube connectable to the open proximal end to create the suction.

37. The endometrial tissue curette of claim 22 further comprises rotation means for rotating the cannula around the longitudinal axis.

38. The endometrial tissue curette of claim 37 in which the rotation means comprises an electrical motor mechanically engageable with a driven gear attached to the cannula near the open proximal end.

39. The endometrial tissue curette of claim 38 in which the rotation means comprises a spin relief coupling proximal to the driven gear and the suction means comprises a vacuum source and tube connectable to the open proximal end to create the suction.

40. The endometrial tissue curette of claim 22 in which the curette has an outside diameter of about 4 millimeters.

41. The endometrial tissue curette of claim 22 in which the curette has an outside diameter of less than about 4 millimeters.

42. The endometrial tissue curette of claim 22 in which each at least one substantially longitudinal elongate slot has a maximum transverse width less than the diameter of the elongate cylindrical hollow bore.

43. The endometrial tissue curette of claim 22 in which the curetting head includes a proximal portion having a bend in the longitudinal axis.

44. The endometrial tissue curette of claim 43 in which the bend is less than about 20°.

45. A method of curetting an endometrial lining of a uterus, the method of curetting comprising the steps of:

providing a hollow cylindrical curette having a distal tip substantially rounded in a longitudinal axis and at least one curetting edge positioned substantially parallel to the longitudinal axis of the hollow cylindrical curette, a portion of the at least one curetting edge extending into the distal tip;

placing the curette into a uterus through the cervical with the at least one curetting edge adjacent the endometrial lining;

suctioning at least a portion of the endometrial lining into the hollow cylindrical curette at the at least one curetting edge position;

curetting the at least a portion of the endometrial lining comprising the step of rotating the hollow cylindrical curette around the longitudinal axis of the hollow cylindrical curette; and removing the curetted endometrial lining with suctioning through the hollow cylindrical curette.

* * * * *

UNITED STATES PATENT AND TRADEMARK OFFICE
CERTIFICATE OF CORRECTION

PATENT NO. : 5,807,282
DATED : September 15, 1998
INVENTOR(S) : Robert Stuart Fowler It is certified that error appears in the above-indentified patent and that said Letters Patent is hereby corrected as shown below:

Column 2, Line 2 delete "effecfiveness" and replace with --effectiveness--.

Column 4, Line 51 after the word "present" and before the word "as" insert --invention--.

Column 4, Line 56 after the word "is" delete the word "sectional" insert --cross-sectional--.

Column 4, Line 63 after the word "as" and before the word "generally" insert --seen--.

Column 6, Line 9 delete the word "usefil" and replace with --useful--.

Column 7, Line 7 after the word "cervical" and before the word "of" insert --os--.

Column 8, Line 62 after the word "adequate" and before the word "especially" delete "curett age" and replace with --curettage--.

Column 8, Line 63 after the word "been" and before the word "achieved" delete the word "maximially" and replace with --maximally--.

Signed and Sealed this

Sixteenth Day of February, 1999

Attest:

Attesting Officer

*Acting Commissioner of Patents and Trademarks*